(12) United States Patent  (10) Patent No.: US 8,709,033 B2
Kim et al.  (45) Date of Patent: Apr. 29, 2014

(54) TRIGGER ACTIVATED LANCET

(75) Inventors: John Kim, Chelsea (CA); James E. Peret, Boylston, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2331 days.

(21) Appl. No.: 11/400,023

(22) Filed: Apr. 7, 2006

(65) Prior Publication Data

US 2006/0259057 A1 Nov. 16, 2006

Related U.S. Application Data

(60) Provisional application No. 60/669,044, filed on Apr. 7, 2005.

(51) Int. Cl.
*A61B 17/32* (2006.01)
(52) U.S. Cl.
USPC ........................................ 606/182
(58) Field of Classification Search
USPC .................. 606/181, 182; 600/583
See application file for complete search history.

(56) References Cited

U.S. PATENT DOCUMENTS

| 4,539,988 | A | * | 9/1985 | Shirley et al. ............... 606/182 |
| 5,133,730 | A | | 7/1992 | Biro et al. |
| 5,397,334 | A | | 3/1995 | Schenk et al. |
| 5,527,334 | A | | 6/1996 | Kanner et al. |
| 5,529,581 | A | * | 6/1996 | Cusack ........................ 606/181 |
| 5,545,174 | A | | 8/1996 | Schenk et al. |
| 5,643,306 | A | | 7/1997 | Schraga |
| 5,782,852 | A | | 7/1998 | Foggia et al. |
| 5,797,940 | A | * | 8/1998 | Mawhirt et al. ............... 606/167 |
| 6,042,595 | A | * | 3/2000 | Morita ........................ 606/181 |
| 6,221,089 | B1 | * | 4/2001 | Mawhirt ..................... 606/181 |
| 6,322,574 | B1 | * | 11/2001 | Lloyd et al. .................. 606/181 |
| 7,160,313 | B2 | * | 1/2007 | Galloway et al. ............. 606/167 |
| 2003/0216767 | A1 | * | 11/2003 | List et al. ..................... 606/181 |
| 2006/0052809 | A1 | | 3/2006 | Karbowniczek |
| 2006/0129173 | A1 | | 6/2006 | Wilkinson |

* cited by examiner

*Primary Examiner* — Thomas McEvoy
*Assistant Examiner* — Julie A Szpira
(74) *Attorney, Agent, or Firm* — The Webb Law Firm

(57) ABSTRACT

A lancet device including a housing and a lancet structure having a puncturing tip maintained within an interior cavity of the housing. The device incorporates a bow spring which cooperates with the lancet structure within the housing, and a trigger which extends laterally through and into the housing. The bow spring is resistive to movement, and therefore maintains the puncturing tip in a retracted position within the housing. Lateral movement of the trigger into the housing, such as through a pivoting trigger operation, biases the bow spring against this resistive to deflect the bow spring and extend the puncturing tip through the forward end of the housing to achieve a puncturing position.

25 Claims, 7 Drawing Sheets

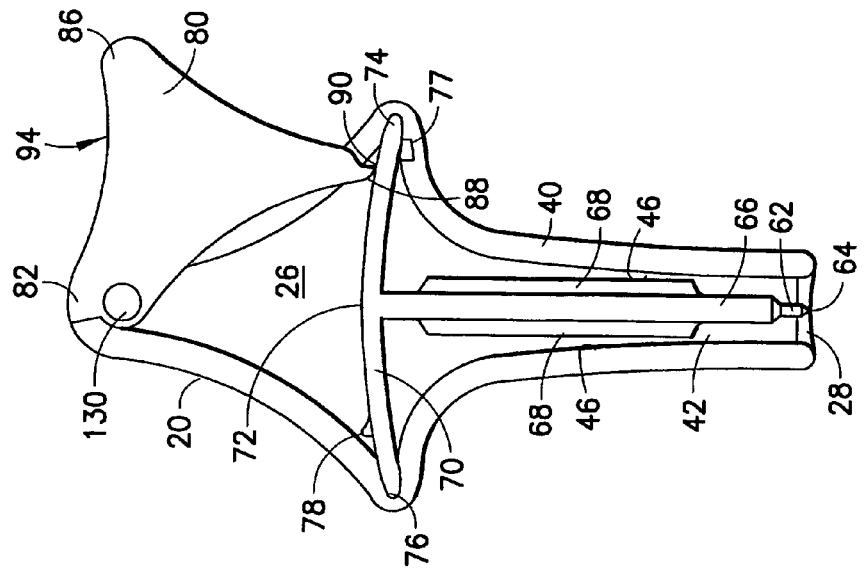
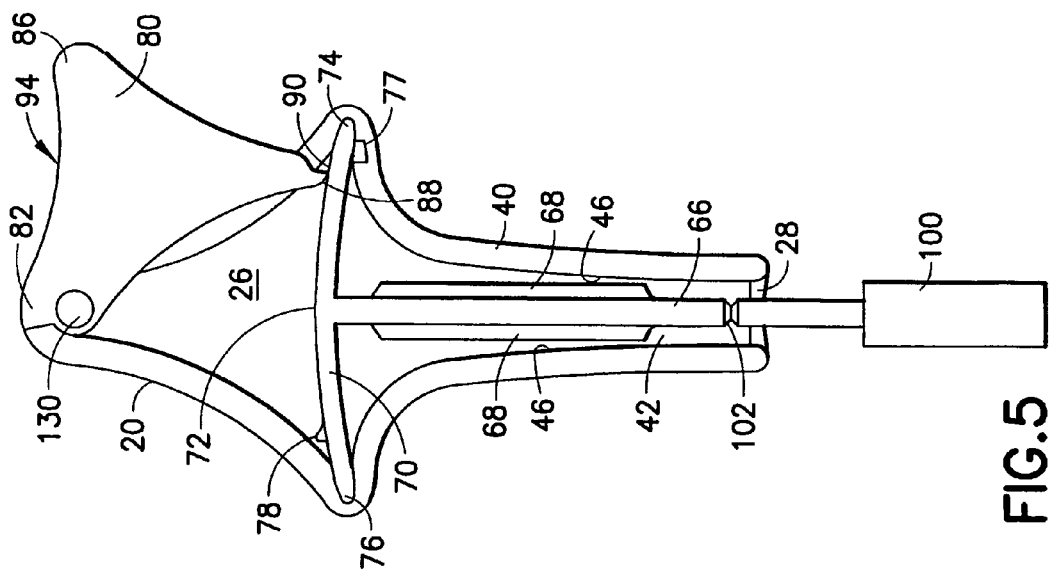

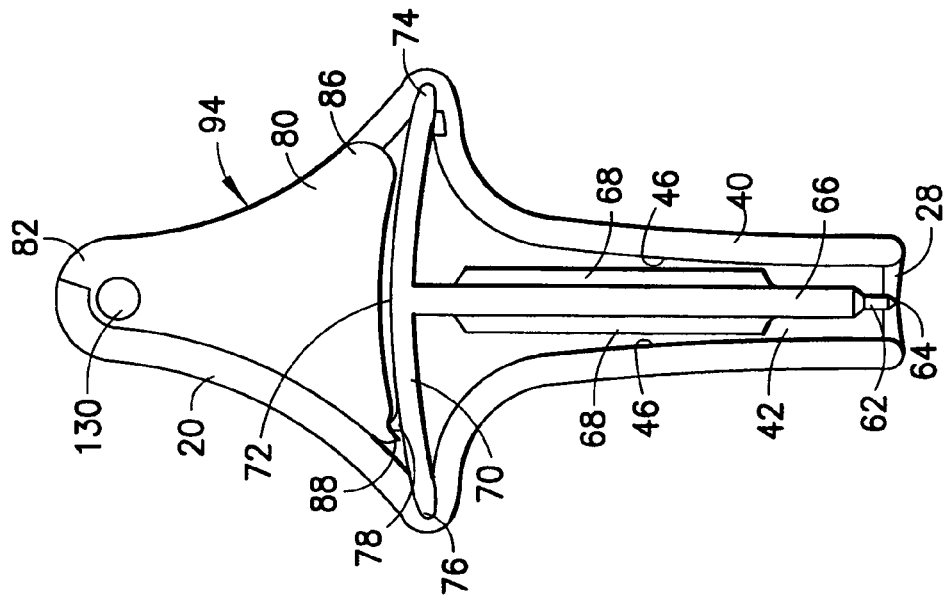
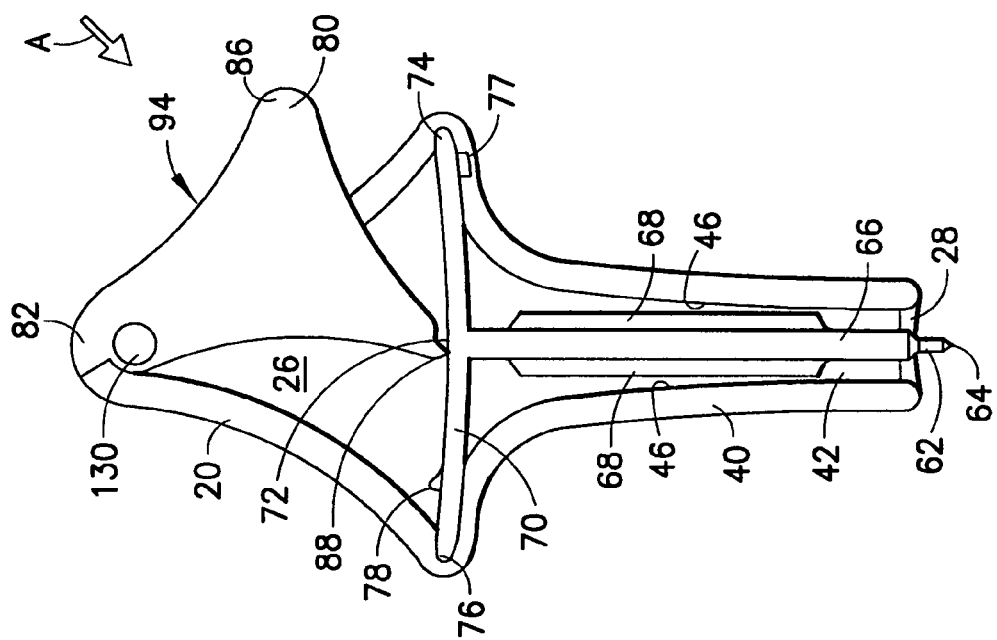

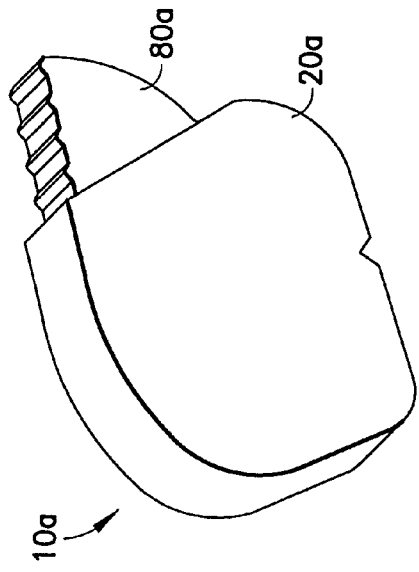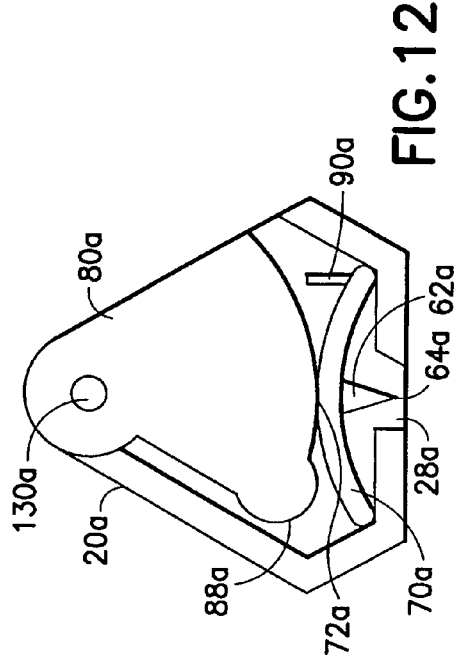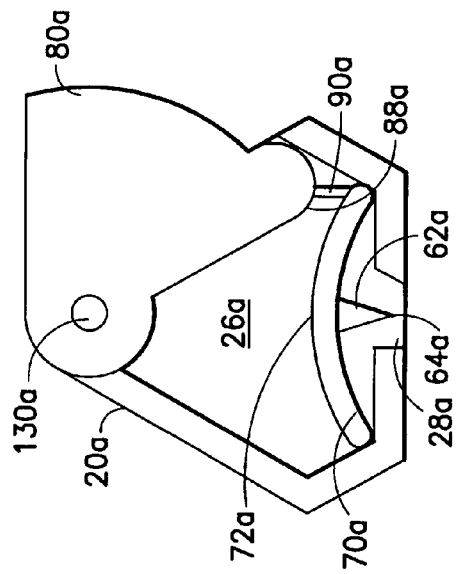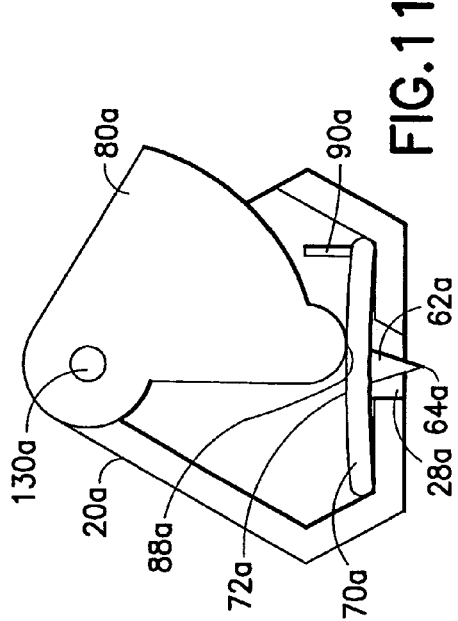

TRIGGER ACTIVATED LANCET

The present application claims the benefit of U.S. Provisional Patent Application No. 60/669,044 as filed on Apr. 7, 2005.

BACKGROUND OF THE INVENTION

1. Field of the Invention

The present invention relates generally to medical puncturing devices, and more specifically to lancets which are used to take blood samples from patients.

2. Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example, on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design involves preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Many such lancet devices involve activation of the puncturing or cutting element during a forward movement motion toward the patient's skin, which can present psychological issues for the patient. As an alternative to such forward activation mechanisms, examples of lateral trigger activated medical puncturing devices are disclosed in U.S. Pat. Nos. 5,527,334; 5,643,306; and 5,133,730. U.S. Pat. No. 5,527,334 to Kanner et al. discloses a complex transmission linkage system for transferring the lateral trigger movement to extend and retract a puncturing needle. U.S. Pat. No. 5,643,306 to Schraga discloses a lancet device with a pivotable spring having a pointed tip such that lateral trigger movement pivots the spring to transfer lateral trigger motion to axial motion of the pointed spring tip. U.S. Pat. No. 5,133,730 to Biro et al. discloses a disposable lancet which includes a pivoting blade means which pivots about a fixed point upon lateral triggering, such that the lateral trigger transverses a slope on the pivoting blade means to pivot the blade to a puncturing position.

U.S. Pat. No. 5,529,581 to Cusack discloses a lancet device which incorporates a cutting blade coupled to the center arch of a curved inversion spring. Axial movement of a pushing element moves the cutting blade and the curved spring forward through the device to a point at which the cutting blade extends through the device to puncture the skin. Continued axial movement of the pushing element contacts the outer edges of the spring to cause the spring to invert upon itself, with the arch of the spring inverting and pulling the cutting blade back within the housing. U.S. Pat. No. 6,322,574 to Lloyd et al. discloses a disposable lancet which includes a T-shaped housing containing a reciprocally movable body extending through a rear end of the housing and having a puncturing needle at the forward end, and with a leaf spring to bias the body toward a safe position with the needle held within the housing. Operation involves pressing the rear portion of the reciprocating body into the housing against the bias of the leaf spring to extend the needle through the forward end of the housing, and releasing the rear portion of the body to permit the leaf spring to retract the needle back within the housing. Such assemblies involve an activation motion which occurs in the general direction of the axis of the lancet device toward the patient's skin, which oftentimes presents psychological issues to the patient.

In view of the foregoing, a need generally exists in the medical field for a simple and reliable disposable medical puncturing device that is easy to manufacture, assemble and use, and which ensures sterility before use and safe and secure disposal after use.

SUMMARY OF THE INVENTION

In accordance with an embodiment of the invention, a lancet device includes a housing including an opening at a forward end thereof and a lancet structure adapted for movement within the housing between a retracted position in which a puncturing end of the lancet structure is maintained within the housing and a puncturing position in which the puncturing end extends through a forward end of the housing. The lancet device further includes a bow spring as a simple beam spring for maintaining the lancet structure in the retracted position when the bow spring is in a first state in which it is resistive to movement. A trigger is adapted for movement in a manner in which a force is applied across a surface of the bow spring, such as lateral movement of the trigger into the housing. Such force applied across the bow spring biases the bow spring against the first state (in which the bow spring is resistive to movement) to a second state in which the bow spring stores energy or is otherwise stressed, thereby extending the lancet structure to the puncturing position.

In one embodiment, the lateral movement of the trigger may involve a pivotal movement of the trigger with respect to the housing. Accordingly, the trigger may be pivotally attached or engaged to the housing, such as at a location substantially opposite the forward end of the housing. In such an arrangement, a distance is defined between the pivot axis and the puncturing end of the lancet structure. Lateral movement of the trigger into the housing, i.e. pivotal movement of the trigger, causes this distance between the pivot axis and the puncturing end of the lancet structure to increase, based on the trigger biasing and deflecting the bow spring.

Desirably, lateral movement of the trigger into the housing biases the bow spring against a state in which the bow spring is resistive to movement, thereby extending the lancet structure to the puncturing position, and subsequently releases the bias against the bow spring. In this manner, the lateral trigger movement causes an initial biasing of the bow spring and a sequential release of the bias against the bow spring, causing it to return toward the condition or state in which it is resistive to movement, thereby retracting the lancet structure to the retracted position. The trigger may preferably be maintained within the housing upon lateral movement of the trigger into the housing, and is desirably locked within the housing upon lateral movement of the trigger into the housing to a position in which the bias against the bow spring is released. In this manner, movement of the trigger out of the housing can only be accomplished through intentional misuse or destruction of the device.

The lancet structure and the bow spring may be unitarily formed or otherwise connected as a unitary structure. Desirably, the bow spring is unitarily molded with one or both of the bow spring and the trigger prior to activation of the lancet device.

The trigger may include a cam surface for camming engagement with the bow spring for biasing the bow spring against the first state. Moreover, the lancet structure may comprise a body extending from one side of an apex of the bow spring. As such, lateral movement of the trigger into the housing causes a portion of the trigger to contact an opposing side of the apex of the bow spring to bias the bow spring against its first state to extend the lancet structure to the puncturing position. The bow spring is desirable fixed with respect to the housing, so as to prevent movement of the bow spring with respect to the housing during movement of the trigger, other than biasing movement of the bow spring.

The trigger may be releasably maintained in a first position with at least a portion of the trigger extending laterally out of the housing, for example, through a connection which plastically yields, deforms or fractures upon lateral movement of the trigger into the housing. In one embodiment, the trigger may be releasably connected to the bow spring through a connection which fractures upon lateral movement of the trigger into the housing. It is contemplated that a connection may be provided between at least two of the elements of the trigger, the bow spring, the lancet structure and the housing, with such a connection adapted to plastically yield, deform or fracture prior to or during initial use of the device. For example, an element may be disposed on one or more of the trigger, the bow spring or the lancet structure, which element is adapted to yield, deform or fracture prior to the lancet structure being extended to the puncturing position.

In a further embodiment of the invention, a lancet device includes a housing including an interior cavity with an opening through the forward end, and an actuation structure maintained within the interior cavity of the housing. The actuation structure includes a bow spring having a puncturing tip extending therefrom. The bow spring is within the housing in a first state, such as one in which it is resistive to movement such as bending or unbending movement, maintaining the puncturing tip in a retracted position within the housing. The device further includes a trigger adapted for movement across a surface of the bow spring in a direction which biases the bow spring away from the first state in which it is resistive to movement, such as through lateral movement of the trigger into the housing. Such force moves the bow spring to a second state, and extends the puncturing tip through the forward end of the housing to achieve a puncturing position. Continued lateral movement of the trigger may subsequently release the bias against the bow spring, permitting the bow spring to return toward the first state, such as by unbending, and retract the puncturing tip to the retracted position. Desirably, the trigger is maintained within the housing upon lateral movement of the trigger into the housing to a position in which the bias against the bow spring is released.

In one embodiment, the trigger is pivotable with respect to the housing, such that lateral movement of the trigger into the housing comprises pivoting the trigger with respect to the housing. This may be accomplished by pivotally connecting the trigger to a pivot hinge at a top portion of the housing, such as at a position generally opposite the puncturing tip. The trigger may comprise a cam surface to provide camming engagement with the bow spring for biasing the bow spring against the first state. Desirably, the trigger is releasably maintained in a first position with at least a portion of the trigger extending laterally out of the housing through a connection that fractures upon lateral movement of the trigger into the housing. For example, the trigger may be integrally molded with the actuation structure as a single structure for assembly with the housing such that the bow spring is maintained within the housing with the puncturing tip extending toward the forward end and the trigger extends laterally from the housing out of the interior cavity of the housing and is connected to the bow spring through a connection which fractures. The device may further include a cover integrally molded over the puncturing tip of the lancet structure.

In yet a further embodiment of the invention, a method of assembling a lancet device includes providing a housing defining an interior cavity and including a substantially closed forward end with an opening extending therethrough, and providing an actuation structure comprising a bow spring having a puncturing tip extending therefrom and a trigger integrally molded thereto through a fracturable connection. The method further comprises inserting the actuation structure into the interior cavity such that the bow spring is maintained within the interior cavity with the puncturing tip directed toward the forward end of the housing and with the trigger extending laterally from the housing. The trigger may then be fixed to the housing in a manner so as to provide for lateral movement into the housing upon fracturing of the fracturable connection. This fixing step may involve connecting the trigger to the housing through a pivotal engagement so as to provide for pivoting movement of the trigger into the housing, such as by closing a portion of the housing so as to fix a portion of the trigger to the housing.

To assist in the molding process and/or to provide structural integrity to the actuation structure, the structure may include a support structure extending between the bow spring and the trigger. In this manner, the method further comprises a step of removing the support structure prior to or immediately after inserting the actuation structure within the housing.

In a further embodiment of the invention, a method of actuating a lancet device includes providing a lancet device including a housing and a bow spring maintained within an interior cavity thereof. The bow spring includes a lancet structure or portion having a puncturing tip extending toward an opening through the forward end of the housing. The lancet device further includes a trigger extending laterally from the housing. The method of actuating involves laterally moving the trigger into the housing so as to bias the bow spring against a first position in which it is resistive to movement, thereby flexing or unbending the bow spring and extending the puncturing tip through the opening in the forward end of the housing to achieve a puncturing position. The laterally moving step may involve pivoting the trigger with respect to the housing.

Desirably, the lancet structure comprises a body extending from one side of an apex of the bow spring. In this manner, laterally moving the trigger involves contacting a surface of the trigger with an opposing side of the apex of the bow spring to bias the bow spring against a state in which it is resistive to movement, thereby extending the lancet structure to the puncturing position. The method may further include a locking step in which the trigger is locked from further movement within the housing after the laterally moving step. Also, the lancet device may include a cover integrally molded with the lancet structure. In this manner, the method further comprises a step of removing the cover prior to moving the trigger.

Further details and advantages of the present invention will become apparent from the following detailed description when read in conjunction with the accompanying drawings.

BRIEF DESCRIPTION OF THE DRAWINGS

FIG. 5 is a cross-sectional view of the lancet device of FIG. 1 in an assembled state prior to use.

FIG. 6 is a cross-sectional view of the lancet device of FIG. 1 with the protective cover removed and ready for use.

FIG. 7 is a cross-sectional view of the lancet device of FIG. 1 in use with the trigger partially depressed and with the lancet structure in the puncturing position.

FIG. 8 is a cross-sectional view of the lancet device of FIG. 1 with the trigger fully depressed and with the lancet structure in the retracted position.

FIG. 9 is a perspective view of a lancet device in accordance with a further embodiment of the present invention.

FIGS. 10-12 are cross-sectional views of the lancet device of FIG. 9 sequentially showing the device ready for use, in use with the trigger partially depressed and with the lancet structure in the puncturing position, and after use with the trigger fully depressed and with the lancet structure in the retracted position, respectively.

DESCRIPTION OF THE PREFERRED EMBODIMENTS

Figure 1:
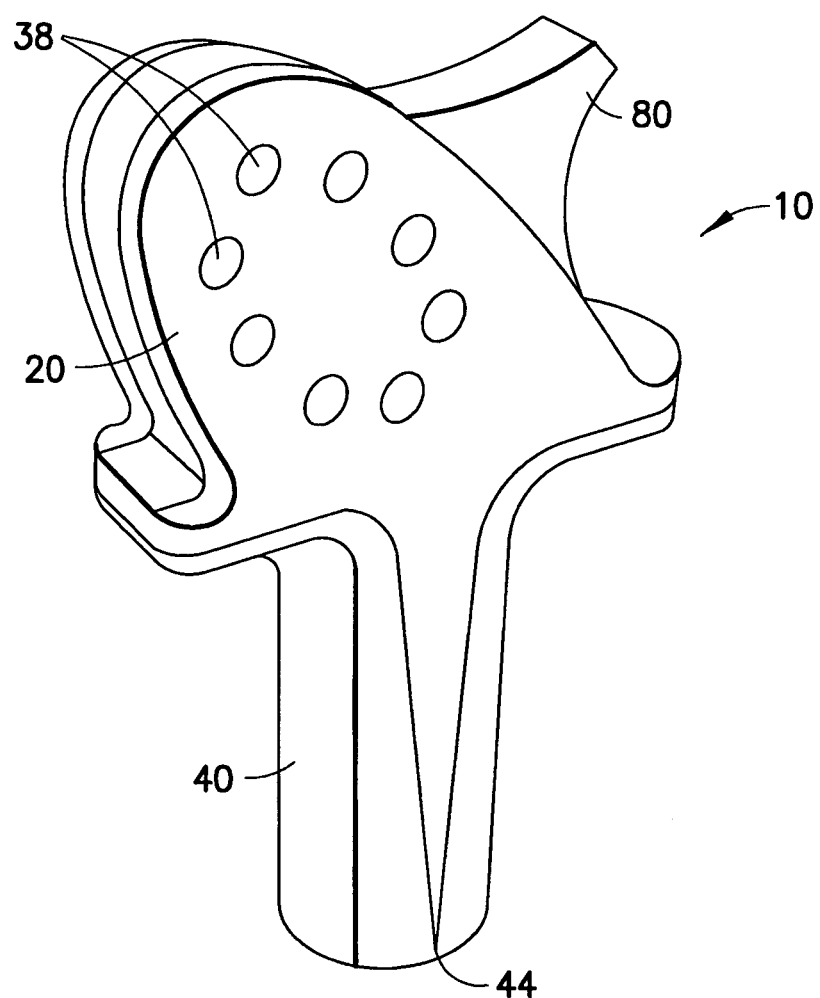
FIG. 1 is a perspective view of a lancet device in accordance with an embodiment of the present invention.

For purposes of the description hereinafter, the words "upper", "lower", "right", "left", "vertical", "horizontal", "top", "bottom", "lateral", "longitudinal" and like terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Referring to FIGS. 1-4, a lancet device 10 according to an embodiment of the invention is generally shown. The lancet device 10 generally includes a main housing body 20, and an actuation structure 61 disposed therein. As will be discussed in greater detail herein, the actuation structure 61 is contained within housing body 20 and includes a lancet portion or structure 60, which is axially movable through the housing body 20 to effect a puncturing operation upon triggering of the lancet device 10. A protective cover 100 is further provided to ensure sterility of the lancet prior to use.

The main housing body 20 defines a generally elongated body extending between a rearward end 22 and a forward end 24. Housing body 20 is a generally closed housing structure defining an interior cavity 26, with a forward opening 28 extending through the forward end 24 through which the lancet structure can extend, as will be discussed in further detail herein. The rearward end 22 of housing body 20 may include an architecture having a rear opening 30, which is particularly useful for assembling the lancet device 10, as will also be discussed in greater detail herein.

In one embodiment as depicted in FIGS. 1-4, housing body 20 defines a generally T-shaped elongated body, including opposing lateral sides 32, 33 having lateral extensions 34, 35 extending therefrom, which may each define a surface for accommodating a user's fingers. Such surfaces may be formed in any profile for accommodating a user's finger, and may further include surface features for providing a tactile feel to the user, such as ribs, grooves, bumps, protrusions, or the like on the outer surface of the housing body 20. Additionally, lateral sides 36, 37 of housing body 20 may also include such surface features for providing a tactile feel to the user, such as bumps 38 on the outer surface of lateral sides 36, 37 of the housing body 20.

Desirably, housing body 20 includes a profile which narrows, generally tapers or is otherwise reduced in size extending toward the forward end 24, such as an elongated body portion 40 defining an internal channel 42 therethrough. In this manner, elongated body portion 40 defines a small contact area about the forward opening 28 for contacting the intended area on the user's body which is to be punctured by the lancet device. The overall architecture of the lancet device as provided through housing body 20 may provide appropriately shaped ergonomical surfaces that substantially conform to a user's fingertips to aid the user in manipulating the lancet device 10 and using the lancet device 10 in a blood letting, drawing, or collection procedure, and may provide multiple finger grip positions for the user. For example, FIG. 1 depicts the lancet device with a generally oblong top portion, which may provide specific ergonomic features to the user during operation of the lancet device.

Lancet device 10 further includes a lancet structure 60 disposed within the housing body 20. As shown through FIGS. 6-8, lancet structure 60 includes a puncturing element, shown in the form of lancet 62 defining a puncturing end 64 at the forward end thereof. Lancet structure 60 is adapted for axial movement through the housing body 20 between an initial position with the puncturing end 64 maintained within the housing body 20 to a puncturing position in which the puncturing end 64 extends beyond the forward opening 28 of housing body 20, as will be discussed further herein in terms of use of the lancet device 10. Puncturing end 64 is adapted for puncturing the skin of a patient, and may define a pointed end, a blade edge, and the like. Puncturing end 64 may also include a preferred alignment orientation, such as with a pointed end of a blade aligned in a specific orientation. In this manner, housing body 20 may include surface indicia, such as alignment point 44, to providing an indication as to proper alignment of puncturing end 64 contained within housing body 20 for use thereof.

Lancet structure 60 may include an elongated body, such as a carrier element 66 supporting lancet 62 at the rearward end thereof. The carrier element 66 and housing body 20 may include corresponding guiding surfaces for guiding the lancet structure 60 therethrough. For example, carrier element 66 may include guide tabs 68 on an external surface thereof, with the elongated body portion 40 of main housing 20 including corresponding guide channels 46 extending longitudinally along an inner surface within internal channel 42 for slidably accommodating guide tabs 68 therein. It is contemplated that other guiding surfaces may also be used. The guide tabs 68 and guide channels 46 ensure that the lancet structure 60 is properly aligned within housing body 20, and provide for sliding axial movement of the lancet structure 60 within the housing body 20, while preventing or resisting rotational movement.

Lancet device 10 further includes a spring mechanism for maintaining the puncturing end 64 of lancet structure 60 within the housing body 20. In particular, bow spring 70 is provided for maintaining lancet structure 60 in the retracted position within housing 20. Bow spring 70 is a simple beam spring, which may be manufactured of a flat bar or strip. Bow spring 70 is adapted to maintain lancet structure 60 in the retracted position based on its tendency to resist movement. More particularly, bow spring 70 is designed so as to hold lancet structure 60 within housing body 20 in a first state in which it is resistive to movement, and to be movable to a second state in when forced or biased against this first state.

Bow spring 70 is supported within housing body 20. For example, first end 74 and second end 76 of bow spring 70 may sit within the interior cavity 26 of housing body 20 at lateral extensions 34, 35, respectively. In this manner, the laterally extending profile of interior cavity 26 can provide supporting shoulder surfaces at lateral extensions 34, 35 for the respective ends 74, 76 of bow spring 70 to sit within. In one embodiment, bow spring 70 is initially formed in a flat state. When supported within housing body 20, bow spring may be bowed or bent into a structure which holds potential energy therein, and maintained within housing body 20 in this state. For example, bow spring 70 may be formed as a resilient structure which extends between first end 74 and second end 76 at a length which is greater than the width of housing body 20 between lateral extensions 34, 35. Accordingly, bow spring 70 is supported within housing body 20 at lateral extensions 34, 35 such that bow spring 70 is charged with an arc at or near the center apex 72 extending between first end 74 and second end 76. In this manner, bow spring 70 provides an arched structure curved away from forward end 24 with the center apex 72 extending toward the rearward end of housing body 20, as shown in FIG. 5, and is resistive to movement out of this shape. Alternately, bow spring 70 in its natural state may be formed as a bent structure with such an arc, such that bow spring 70 has a natural tendency to maintain this bowed or bent state and is resistive to movement out of this shape. In any event, bow spring 70 is adapted to be maintained within housing body 20 in a manner in which it is resistive to movement out of such a bent or bowed shape when it is present within the interior cavity 26 of housing body 20.

Bow spring 70 may be integrally molded, fixedly attached or otherwise adhered to main body 20, such as through a mechanical frictional engagement or an appropriate adhesive. In one embodiment, bow spring 70 includes a protrusion for interference engagement with housing body 20 when bow spring 70 is supported therein. For example, bow spring 70 may include an anchor 77 extending from the lower portion thereof adjacent first end 74. With bow spring 70 positioned within housing body 20, anchor 77 rests within a pocket or recess 39 within the wall of housing body 20. In this manner, bow spring 70, and in particular the first end 74 of bow spring 70, is completely restrained from movement, namely lateral movement, during use of the device, as will be described in further detail herein.

Figure 2:
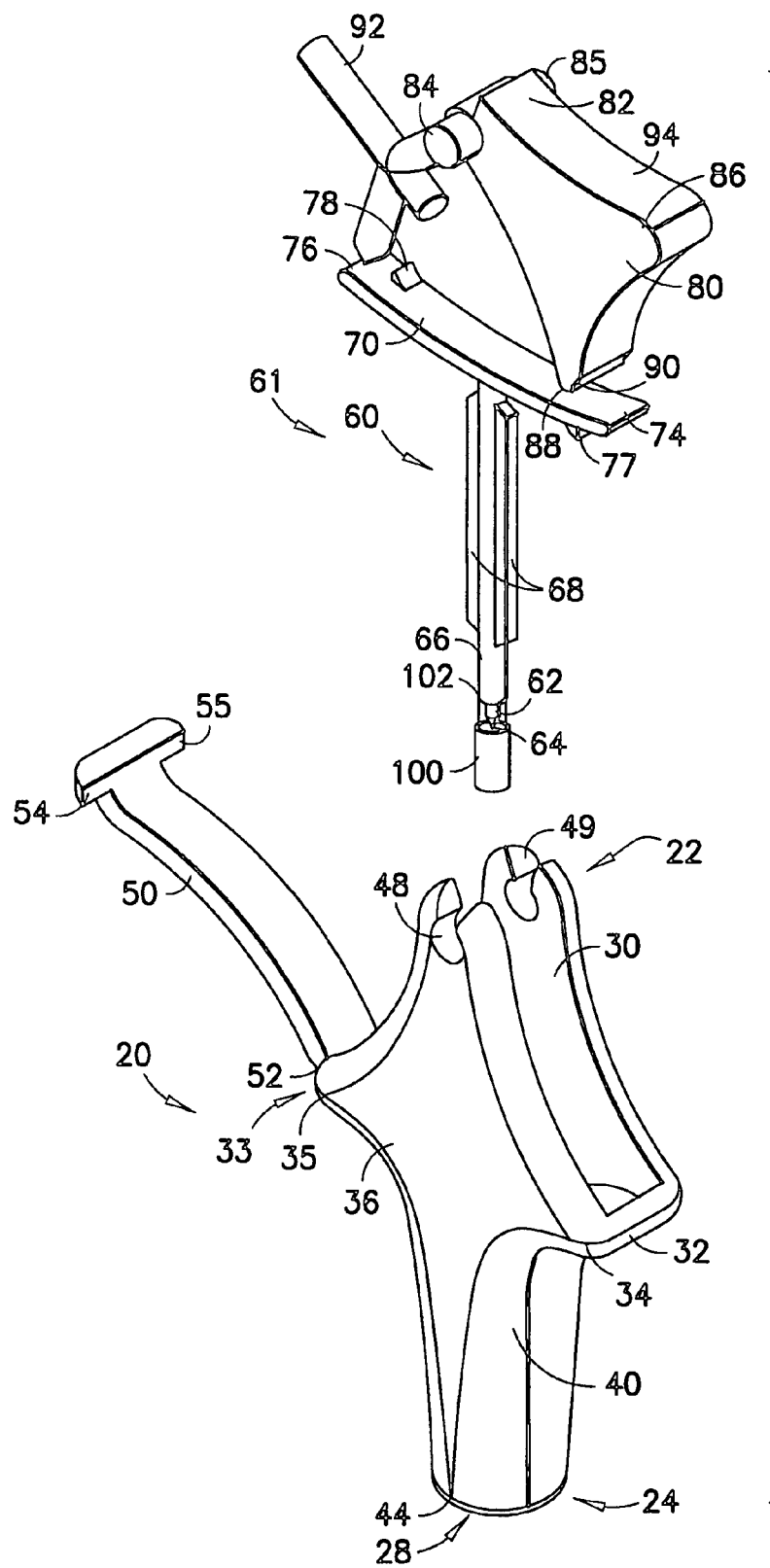
FIG. 2 is an exploded perspective view of the lancet device of FIG. 1 during assembly.
Figure 3:
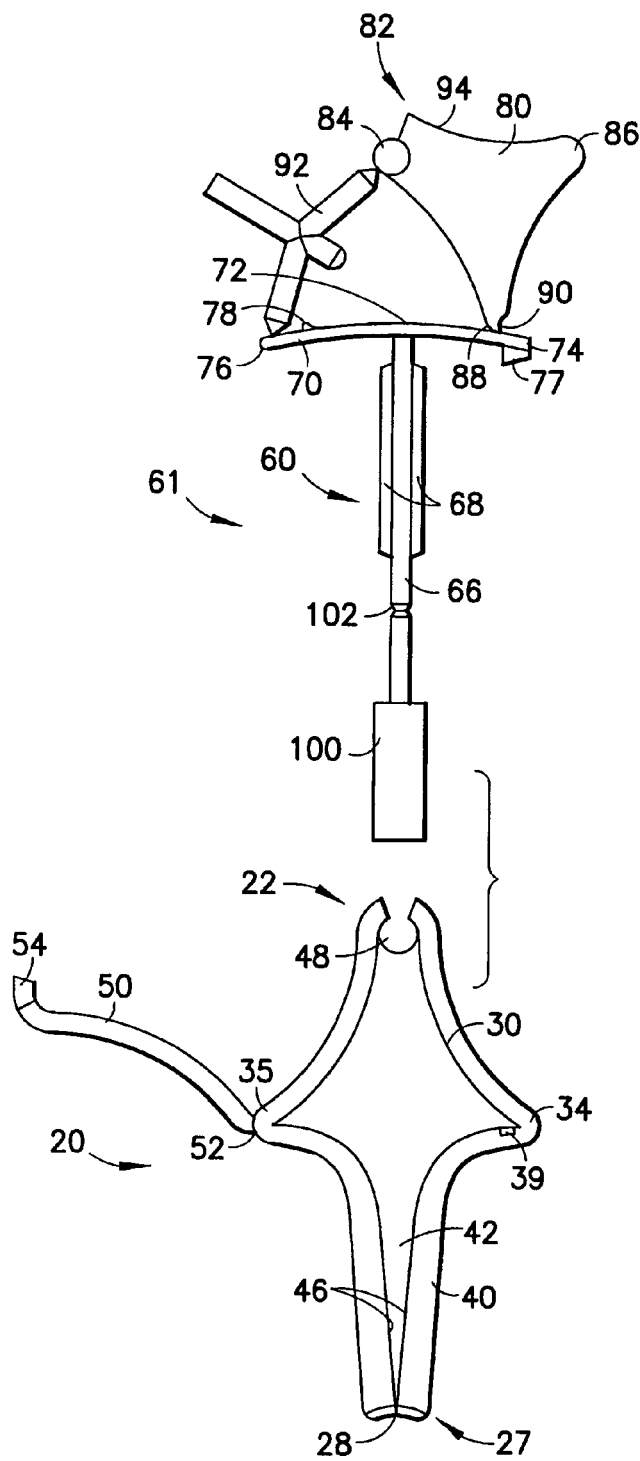
FIG. 3 is an exploded front view of the lancet device of FIG. 2 during assembly.
Figure 4:
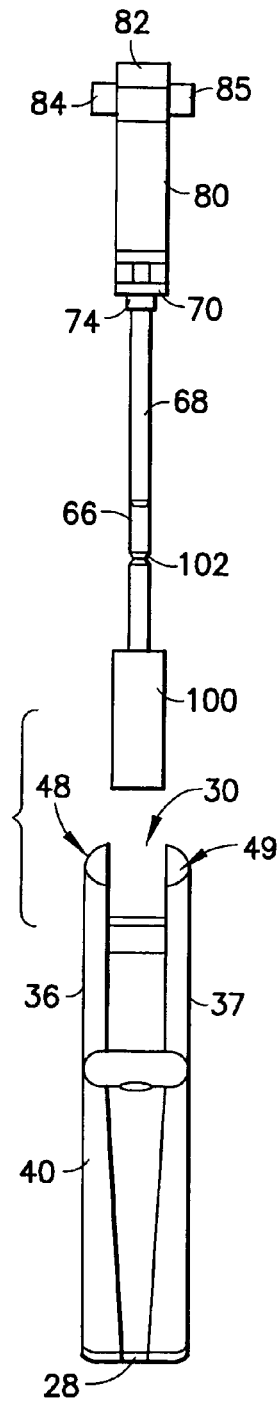
FIG. 4 is an exploded side view of the lancet device of FIG. 2 during assembly.
Figure 13:
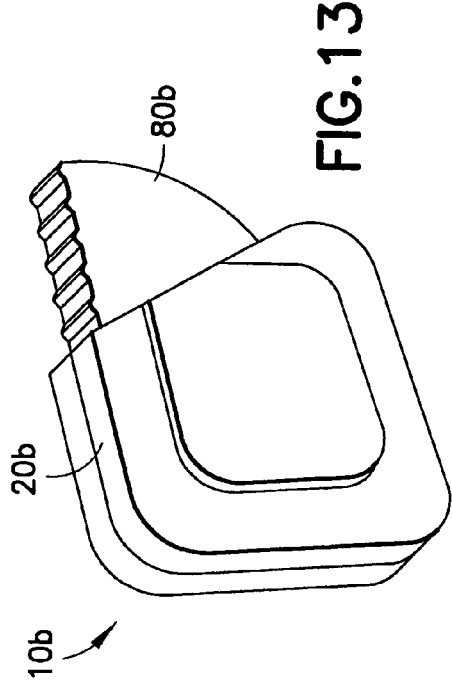
FIG. 13 is a perspective view of a lancet device in accordance with yet further embodiment of the present invention.
Figure 16:
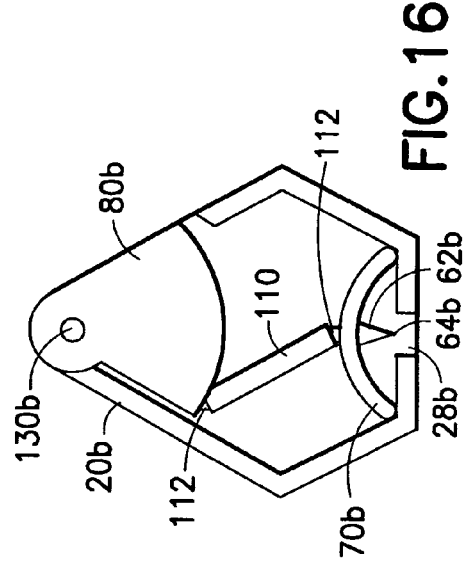
FIGS. 14-16 are cross-sectional views of the lancet device of FIG. 13 sequentially showing the device ready for use, in use with the trigger partially depressed and with the lancet structure in the puncturing position, and after use with the trigger fully depressed and with the lancet structure in the retracted position, respectively.
Figure 14:
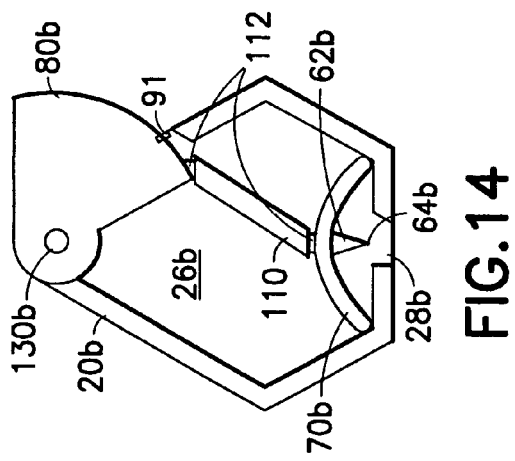
Figure 15:
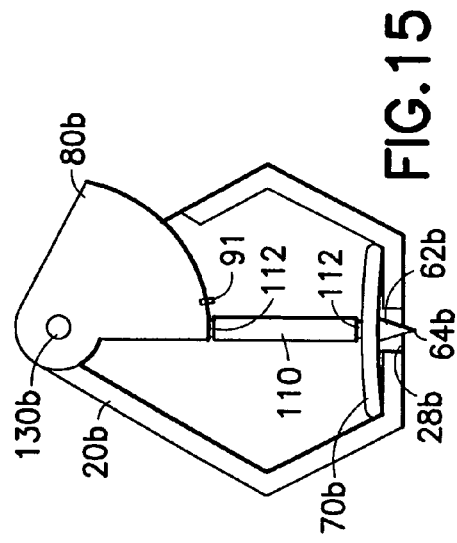

Bow spring 70 provides a mechanism for holding and retracting lancet structure 60 in a retracted position within housing body 20. Accordingly, lancet structure 60 and bow spring 70 are in a fixed relation, such that movement of the bow spring 70 results in movement of the lancet structure 60. Bow spring 70 and lancet structure 60 may be separate structures which are attached together, or may be integrally molded, as shown in the embodiment of FIGS. 2-4, in which bow spring 70 is integrally molded with the lancet structure 60. With bow spring 70 and lancet structure 60 unitarily molded or otherwise connected, an actuation structure 61 is formed. In this manner, the bow spring 70 is adapted to maintain the lancet structure 60 within the housing body 20 and to retract the lancet structure 60 within the housing body 20 after the lancet structure 60 is axially moved to the puncturing position. In the embodiment depicted in FIGS. 2-4, bow spring 70 represents a bowed or bent spring structure within housing body 20, with apex 72 formed from the curvature of the natural arc of bow spring 70 on one side thereof, and the lancet carrier element 66 extending from the other side at a bottom surface of bow spring 70 opposite apex 72.

With bow spring 70 maintaining the puncturing end 64 of lancet structure 60 within the housing body 20, lancet device 10 further includes a mechanism for driving the lancet structure 60 to the puncturing position in which the puncturing element at puncturing end 64 of lancet 62 extends through the opening 28 at forward end 24 of housing body 20. In particular, lancet device 10 further includes an actuator, such as trigger 80, which is adapted for movement with respect to housing body 20 so as to force bow spring 70 against its bowed or bent state in which it is resistive to movement, to drive the lancet structure 60 to the puncturing position. Trigger 80 extends laterally out of housing body 20 and is adapted for lateral movement into housing body 20 so as to bias the bow spring 70 against its natural state. Such movement provides a mechanism for forcing or driving movement of the lancet structure 60 through housing body 20 to the puncturing position against any retaining force of the bow spring 70 which holds the lancet within housing body 20.

More particularly, trigger 80 extends through housing body 20 and into interior cavity 26 therein, such as through one of the opposing lateral sides 32, 33. The profile and architecture of trigger 80 is designed such that lateral movement of trigger 80 into housing body 20 through one of the lateral sides 32, 33 causes trigger 80 to contact the bow spring 70. For example, trigger 80 may include an engagement surface for contacting the apex 72 of bow spring 70 as trigger 80 moves laterally into housing body 20. Such contacting is accomplished with sufficient force so as to bend or otherwise displace bow spring 80 against its bowed or bent state in which it is resistive to being unbent.

Movement of trigger 80 is described herein in terms of lateral movement. Lateral movement is intended to encompass any movement of the actuator or trigger in a direction other than parallel to the lancet axis, i.e., the axis of movement of the lancet to the puncturing position. For example, lateral movement may contemplate a sideways movement of the trigger through the housing body in a direction substantially perpendicular to the axis of the lancet movement, may contemplate a pivotal movement of the trigger through the side of the housing body, or other non-axial movement with respect to housing body 20.

In a particular embodiment of the invention as shown, for example, in FIGS. 2-8, trigger 80 is in pivotal engagement with housing body 20. In particular, trigger 80 may include a pivot end 82 including pivot rods 84, 85 extending laterally from opposing sides thereof. Housing body 20 may include a pair of corresponding hinge pockets 48, 49 at the rearward end thereof, for accommodating the pivot rods 84, 85 of trigger 80 in pivotal engagement therein. Pivot rods 84, 85 are set within hinge pockets 48, 49 such that at least a portion of trigger 80, such as trigger extension 86, extends out from housing body 20.

Trigger extension 86 may be ergonomically shaped or formed so as to conform to a user's finger, and may include a finger grip indentation 94 on the outer surface thereof in this manner. Moreover, finger grip indentation 94 may include a tactile surface for the user, such as bumps or ridges to prevent sliding of the finger therealong during use. A portion of trigger 80 which extends within housing 20 opposite the trigger extension 86 includes engagement surface 88 for contacting bow spring 70 as trigger 80 moves laterally within housing body 20, as will be discussed in more detail herein in terms of use of the lancet device 10. In one particular embodiment, trigger 80 is shaped in a generally triangular form, as depicted in FIG. 5. In such an embodiment, the top of the triangle forms the pivot point with respect to the housing, one of the bottom points of the triangle forms the trigger extension extending out from the housing, and the other bottom point of the triangle extends within the housing and includes the engagement surface for contacting and biasing the bow spring.

The interference engagement between the engagement surface 88 of trigger 80 and the bow spring 70 provides the force or driving movement for driving the lancet structure 60 to the puncturing position. The bow spring 70 is sufficiently resilient so as to be maintained within housing body 20 in a first state in which it resists movement toward an unbent or unbowed condition, yet is bendable upon application of a force across apex 72 through engagement surface 88 so as to be biased or inverted against this first state. Moreover, the resilient nature of the bow spring 70 permits it to at least partially return to this first state in which it is resistive to movement, such as a bowed state, after the force across apex 72 is released, thereby maintaining puncturing end 64 from protruding through housing body 20.

Trigger 80 may be releasably maintained in a first position prior to use with trigger extension 86 extending outwardly from lateral side 32 of housing body 20. This may be accomplished through an interference engagement between trigger 80 and a portion of housing body 20 or bow spring 70. In one embodiment, trigger 80 may be interconnected to housing body 20 or bow spring 70 through a connection which plastically yields, deforms or fractures upon application of a predetermined force or torque to trigger 80 such as through lateral or pivotal movement thereof. In one embodiment as depicted in FIGS. 2-4, trigger 80 may be integrally formed with bow spring 70 through a fracturable connection 90.

Moreover, lancet device 10 may include structure so as to prevent trigger 80 from moving out of housing body 20 after it has moved laterally therein. This may be accomplished by the overall profile of trigger 80, or may involve specific structure which interferes to prevent a reverse movement of trigger 80. For example, lancet device 10 may include an interference engagement between trigger 80 and either housing body 20 or bow spring 70, such as a ratchet-like interference engagement wherein pivotal movement of the trigger with respect to the housing is generally unidirectional in the absence of misuse or intentional destruction. In one embodiment, bow spring 70 may include a protrusion 78 for interference engagement with a portion of trigger 80, such as engagement surface 88, to prevent a return movement of trigger 80 out of housing body 20.

Lancet device 10 may further include a protective cover for protectively covering the puncturing end 64 of the lancet structure 60 prior to use thereof in order to maintain sterility. The protective cover defines a cover body 100 which may extend within the opening 28 of the housing body 20, thereby protectively surrounding and encompassing at least a portion of the puncturing element, namely lancet 62. Cover body 100 is desirably formed integrally with carrier element 66 of lancet structure 60, completely encompassing lancet 62, thereby maintaining sterility thereof prior to use. Cover body 100 and carrier element 66 may include a notched portion 102 at a juncture therebetween, providing a fraction point for cover body 100 and exposing lancet 62. Alternatively, the cover body 100 may be secured directly to the lancet 62 by methods customary in the medical field, such as with a releasable medical grade adhesive.

The respective elements of the lancet device in one embodiment of the invention are all typically formed of molded plastic material, such as a medical grade plastic material. The lancet 62 may be constructed of any suitable material adapted for puncturing the skin, and is typically a surgical grade metal such as stainless steel. The bow spring 70 may be constructed of any suitable material, such as a plastic or metallic material, and may be insert molded with the lancet structure 60 or may be integrally molded therewith. Desirably, the lancet device is assembled from two separate structures as depicted in FIGS. 2-4, namely a housing portion and an activation portion to be inserted therein. For example, the housing body 20 is desirably provided as a molded structure extending between the rearward end 22 and the forward end 24 to define the interior cavity 26 with forward opening 28. Housing body 20 is desirably molded with the rearward end being open-ended, and with flap 50 integrally molded to housing body 20 through a living hinge 52.

The actuation structure 61 is desirably provided as a separate insert molded structure with the lancet 62 insert molded within the lancet structure 60, and including the lancet carrier 66 and the cover body 100 integrally molded thereover. Desirably, the bow spring 70 and the trigger 80 are also integrally molded with the lancet structure 60, providing actuation structure 61 as a simple one-piece molded structure. In such an embodiment, trigger 80 is integrally molded to bow spring 70 through fracturable connection 90. Additionally, a support structure 92 may be formed between the trigger 80 and the bow spring 70 during the molding procedure. Such a support structure 92 is merely provided as structural reinforcement during the molding and assembly procedure, and is not intended to be used within the lancet device after assembly.

Actuation structure 61 provided as such can be inserted within housing body 20 through the rear opening 30 at rearward end 22 such that the cover body 100 extends through the forward opening 28, with first end 74 and second end 76 of bow spring 70 resting within pockets created within the interior cavity 26 at lateral extensions 34 and 35, respectively. Actuation structure 61 is fully inserted within housing body 20 such that anchor 77 at first end 74 of bow spring 70 is inserted within the pocket or recess 39 of housing body 20 and pivot rods 84, 85 on opposing lateral sides of the pivot end 82 of trigger 80 snap fit within the hinge pockets 48, 49 of housing body 20. Support structure 92 can then be broken away from its connection between trigger 80 and bow spring 70. Flap 50 of housing body 20 can then be closed about living hinge 52, and laterally extending fingers 54, 55 on the end edge of flap 50 can be snap fit or otherwise fixed into the hinge pockets 48, 49, thereby closing pivot rods 84, 85 within hinge pockets 48, 49 and providing for pivotal rotation therein. Trigger 80 extends laterally through the side of housing body 20 through the remainder of rear opening 30 that is opposite the flap 50. Trigger 80 completely encloses this opening, providing for an entirely enclosed lancet device 10 with trigger 80 extending laterally out of housing body 20.

In an alternate embodiment, the housing body may be provided as a fold-over structure. In particular, the housing body may be provided with the opposing lateral sides being interconnected along one edge thereof through a living hinge, creating a folding housing structure. In this manner, the actuation structure 61 can be inserted within the housing body while in an opened state, and the housing body can then be folded over by folding the two lateral sides toward each other along the living hinge. The lateral sides may then be fixed together, such as through a snap-fit arrangement, thereby fixing the actuation structure within the enclosed housing body formed in this manner.

Use of the lancet device 10 will now be described with general reference to FIGS. 1-8, and particular reference to FIGS. 5-8. Prior to use, lancet device 10 is provided as shown in FIGS. 1 and 5 with protective cover body 100 covering the puncturing end 64 of lancet 62. Lancet device 10, and in particular actuation structure 61, is in an initial pre-activation state, with bow spring 70 in its resistive state bent within interior cavity 26 of housing body 20. In this manner, the bow spring 70 is curved such that the apex 72 extends toward the rearward end 22 of housing body 20. The carrier element 66 of lancet structure 60 extends from the bottom surface of bow spring 70 opposite the apex 72, with the cover body 100 extending through forward opening 28 and with the lancet puncturing end 64 contained within cover body 100 at a position retracted behind or within forward opening 28.

To prepare the lancet assembly for use, the user grasps housing body 20, such as between a finger and thumb on opposing sides 36, 37 using bumps 38 as a tactile indicator, and removes the protective cover body 100 from the forward end as shown in FIG. 6, thereby exposing the puncturing end 64 of lancet 62 within housing body 20. The cover body 100 may be ergonomically formed for easy manipulation to allow the user to apply the necessary force to break the cover body 100 from the carrier element 66 at the notch 102 to thereby release the cover body 100 from the lancet 62. The applied breaking force may be a singular twisting or pulling motion, or a combined "twisting" (i.e. rotational) and "pulling" motion applied for breaking the connection between the cover body 100 and the carrier element 66. The resilient nature of bow spring 70 prevents the bow spring 70 from bending or inverting out of its first resistive state during removal of the protective cover body 100 in this manner, and ensures that the bow spring 70 returns to this state in the event that it is flexed, unbent or inverted during this cover removal process.

The forward end 24 of the housing body 20 may then be contacted with a location on the skin surface of a user's body or another person's body where it is desired to initiate blood flow. If provided, target indicia on the lancet device 10 such as alignment point 44 may be aligned with the desired location of puncture.

Once placed against the body, the user exerts a laterally directed force on the trigger 80 while maintaining housing body 20 against that skin surface. In the particular embodiment depicted in the figures, the user applies a force against the finger grip indentation 94 of trigger extension 86, in the general direction of arrow A of FIG. 7. The profile and architecture of lancet device 10 with trigger 80 provides for such a lateral force to include a slight downward force element in addition to the lateral force element, thereby ensuring that the lancet device 10 is maintained against the patient's skin surface.

The initial lateral force applied against the outer surface of trigger extension 86 causes fracturable connection 90 between trigger 80 and bow spring 70 to fracture, thereby releasing the trigger 80 from the initial position with trigger extension 86 extending laterally from housing body 20. Ideally, the strength of the fracturable connection 90 requires a significant amount of force to fracture, which is stored as potential energy when applied by the user on the trigger 80. In this manner, the force applied to trigger 80 which causes fracturable connection 90 to fracture carries a momentum which results in continued movement of trigger 80 into housing body 20 based on the initial force.

Such momentum, coupled with continued application of lateral force against the outer surface of trigger extension 86 after fracturable connection 90 fractures, causes trigger 80 to pivot with respect to housing body 20 about a pivot hinge 130 provided through the engagement of pivot rods 84, 85 within pivot hinge pockets 48, 49. The transfer of the stored potential energy into kinetic energy sufficient to provide pivotal movement of trigger 80 causes engagement surface 88 of trigger 80 to ride along the top surface of bow spring 70, establishing a cam-like engagement between the engagement surface 88 of trigger 80 and the top surface of bow spring 70. The interference engagement provided between bow spring 70 and housing body 20 through anchor 77 resting within recess 39 assists in stabilizing and anchoring bow spring 70 within housing body 20 to restrain the bow spring 70. In particular, the force applied against the top surface of bow spring 70 through the cam-like engagement with the engagement surface 88 of trigger 80 tends to push bow spring 70 laterally within housing body 20 in a sliding manner, establishing a tendency for the first end 74 of bow spring 70 to compress toward the second end 76 and/or to lift up within housing body 20. Anchor 77 within recess 39 provides an interference engagement between bow spring 70 and housing body 20, thereby preventing such movement and anchoring or relieving the tendency of the first end 74 of bow spring 70 to travel or lift.

During movement of trigger 80 into housing body 20 and while engagement surface 88 passes across apex 72 of bow spring 70, sufficient force which may be based on the energy released from the fracturing of the fracturable connection 90 is applied against bow spring 70 from the engagement surface 88 to cause bow spring 70 to temporarily flex, flatten, unbend, or invert, thereby biasing or deflecting bow spring 70 against its initial resistive state toward a second state such that apex 72 is directed toward the forward end 24 of housing body 20. Since lancet carrier element 66 is attached with bow spring 70, this biasing of bow spring 70 transfers movement to the lancet carrier element 66, causing axial sliding movement of lancet carrier element 66 toward the forward end 24 of housing body 20.

The corresponding guiding surfaces provided through guide tabs 68 and guide channels 46 guide the lancet carrier element 66 through the elongated body portion 40 of the housing body 40, ensuring proper axial alignment therebetween. In this manner, lancet carrier element 66 is guided axially through the housing body 20 toward the forward end 24 and toward the skin surface based on the force applied to the trigger 80, in turn causing the puncturing end 64 of lancet structure 60 to be driven through housing body 20 to a puncturing position, in which puncturing end 64 of lancet 62 extends through the forward opening 28 at a sufficient distance to force the puncturing end 24 to puncture the patient's skin surface.

Continued lateral movement of trigger 80 causes engagement surface 88 to ride along the top surface of bow spring 70 past the apex 72 to a point at which engagement surface 88 is no longer in direct contact with at least the apex 72 of bow spring 70. The resilient nature of bow spring 88 causes bow spring 70 to return to its resistive condition, such that the apex 72 of bow spring 70 is once again directed toward the rearward end 22 of housing body 20. This return movement of bow spring 70 causes the lancet carrier element 66 to retract back through the housing body 20 based on the resiliency of bow spring 70, such that the lancet puncturing end 64 retracts back through the forward opening 28 through forward end 24, to a retracted position shielded within the elongated body portion 40 of housing body 20.

Moreover, during such continued lateral movement of trigger 80 within housing body 20, engagement surface 88 rides across protrusion 78 on the top surface of bow spring 70. An interference engagement is thereby established between engagement surface 88 of trigger 80 and protrusion 78 of bow spring 70 within housing body 20, thereby locking the trigger 80 within the housing body 20 with lancet structure 60 retracted therein, and preventing further movement of lancet structure 60 to the puncturing position.

Moreover, the profile of finger grip indentation 94 of trigger extension 86 may be designed so as to match the external profile of lateral side 32 of housing body 20, thereby entirely closing off the rear opening 30 of housing body 20 and providing a clear visual indicator that the lancet device has been used and preventing any mechanism for further movement. The lancet device 10 is therefore safely protected from re-use and may be properly discarded, such as in an appropriate medical waste container.

Alternately, the profile and size of the finger grip indentation 94 of trigger extension 86 may be designed so that movement of trigger 80 into housing body 20 renders trigger 80 difficult to access by a user's fingers, thereby essentially rendering the device incapable of repositioning the trigger in the absence of deliberate or excessive manipulation to do so.

While activation of the device is described herein in a stepwise fashion, it is noted that puncturing of the skin and retraction of the lancet, in the described embodiment, occur almost instantaneously due to the design of the device, choice of materials, and the tolerance of the materials. As such, while it is the actual lateral pressure applied by the user which is directly transferred to force the lancet to puncture the skin surface, the retraction is also based upon such application of force, in that continued application of such lateral force or torque permits the bow spring to deflect, retracting the lancet back within the housing. Therefore, in the described embodiment, activation of the device including piercing and retraction occur almost simultaneously in a single operation. The lancet device of the present embodiment therefore provides an effective and economical structure which is easy to manufacture and assemble and which is safely protected from re-use.

FIGS. 9-16 depict further embodiments of the present invention that include many components which are substantially identical to the components of FIGS. 1-8. Accordingly, similar components performing similar functions will be numbered identically to those components of FIGS. 1-8 except that a suffix "a" will be used to identify those similar components in FIGS. 9-12, and a suffix "b" will be used to identify those similar components in FIGS. 13-16.

In the alternate embodiment of FIGS. 9-12, lancet device 10a includes similar structure as that described with respect to FIGS. 1-8. However, the housing body 20a of lancet device 10a is more compact and less elongated, eliminating elongated body portion 40 of housing body 20 as in the previous embodiment, and thereby eliminating the corresponding elongated body of lancet carrier element 66. In the embodiment of FIGS. 9-12, lancet 62a with puncturing end 64a is directly attached to or molded with bow spring 70a. As shown through FIGS. 10-12, use of the lancet device 10a involves laterally depressing trigger 80a. Initial depressing of trigger 80a causes fracturable connection 90a to fracture, releasing trigger 80a for movement. Continued depressing of trigger 80a results in pivoting of trigger 80a about pivot hinge 130a, thereby moving trigger 80a laterally into the interior cavity 26a within housing body 20a.

As trigger 80a moves laterally therein, engagement surface 88a of trigger 80a contacts and cams against the top surface of bow spring 70a, thereby bending bow spring 70a as the engagement surface 88a passes over the apex 72a. Such bending extends lancet 62a downward toward forward opening 28a, to a position in which puncturing end 64a extends through forward opening 28a to a puncturing position. Further lateral movement of trigger 80a causes engagement surface 88a to pass beyond apex 72a, thereby releasing the biasing force against bow spring 70a, and permitting bow spring 70a to return to its natural bowed state. Such return movement draws the puncturing end 64a of lancet 62a back within forward opening 28a, thereby retracting the lancet within housing body 20a. The overall profile and architecture of trigger 80a and housing body 20a may be designed so as to prevent the trigger 80a from being pulled out of housing body 20a, to prevent reuse of the lancet device.

In the embodiment of FIGS. 13-16, lancet device 10b includes similar structure and components as described in connection with the embodiments of FIGS. 1-8 and FIGS. 9-12. As with the embodiment of FIGS. 9-12, lancet 62b with puncturing end 64b is directly attached to or molded with bow spring 70b. However, lancet structure 10b further includes a linkage 110 extending between the trigger 80b and the bow spring 70b for causing bending of the bow spring 70b against its bias. In particular, a portion of trigger 80b which extends within the interior cavity 26b of housing body 20b is interconnected with the top portion of bow spring 70b at the apex thereof through a linkage 110 by way of hinges 112. As shown through FIGS. 14-16, use of the lancet device 10b involves laterally depressing trigger 80b. Initial depressing of trigger 80b causes a fracturable connection 91 which extends between trigger 80b and housing body 20b to fracture, releasing trigger 80b for movement. Continued depressing of trigger 80b results in pivoting of trigger 80b about pivot hinge 130b, thereby moving trigger 80b laterally into the interior cavity 26b within housing body 20b.

As trigger 80b moves laterally therein, hinges 112 bend, thereby deflecting linkage 110. Such deflection applies a force against the top surface of bow spring 70b, thereby bending bow spring 70b as the trigger 80b is partially depressed laterally within housing 20b. Such bending of bow spring 70b extends lancet 62b downward toward forward opening 28b to a position in which puncturing end 64b extends through forward opening 28b to a puncturing position. Further lateral movement of trigger 80b causes hinges 112 to continue to bend, thereby deflecting linkage 110 to deflect beyond its center point parallel with the axis of movement of lancet 62b. Such movement releases the biasing force against bow spring 70b, thereby permitting bow spring 70b to return to its natural bowed state. Such return movement draws the puncturing end 64b of lancet 62b back within forward opening 28b, thereby retracting the lancet within housing body 20b. The overall profile and architecture of trigger 80b and housing body 20b may be designed so as to prevent the trigger 80b from being pulled out of housing body 20b, to prevent reuse of the lancet device.

The lancet devices as described herein are preferred embodiments of the invention, and those skilled in the art may make modifications and alterations without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lancet device comprising:
    a housing including an opening at a forward end thereof;
    a lancet structure comprising a puncturing end, the lancet structure adapted for movement within the housing between a retracted position with the puncturing end within the housing and a puncturing position with the puncturing end extending through a forward end of the housing;
    a bow spring maintaining the lancet structure in the retracted position in a first state; and
    a trigger adapted for lateral movement into the housing, wherein lateral movement of the trigger into the housing biases the bow spring from the first state to a second state, thereby extending the lancet structure to the puncturing position.

2. A lancet device as in claim 1, wherein lateral movement of the trigger into the housing causes the trigger to travel across at least a portion of the bow spring.

3. A lancet device as in claim 1, wherein the trigger is pivotable with respect to the housing, and wherein lateral movement of the trigger into the housing comprises pivoting the trigger to with respect to the housing.

4. A lancet device as in claim 1, wherein the lancet structure momentarily extends to the puncturing position upon lateral movement of the trigger.

5. A lancet device as in claim 1, wherein the trigger is pivotable with respect to the housing enabling the lateral movement of the trigger.

6. A lancet device as in claim 1, wherein the trigger is maintained within the housing upon lateral movement of the trigger into the housing.

7. A lancet device as in claim 1, wherein the trigger is maintained encapsulated by the housing after activation.

8. A lancet device as in claim 1, wherein the first state of the bow spring is its natural state, and wherein lateral movement of the trigger into the housing biases the bow spring against its natural state to extend the lancet structure to the puncturing position.

9. A lancet device as in claim 8, wherein lateral movement of the trigger into the housing biases the bow spring against its natural state and subsequently releases the bias against the bow spring, permitting the bow spring to return to its natural state thereby retracting the lancet structure to the retracted position.

10. A lancet device as in claim 9, wherein the trigger is maintained within the housing upon lateral movement of the trigger into the housing to a position in which the bias against the bow spring is released.

11. A lancet device as in claim 1, wherein the trigger comprises a cam surface for canning engagement with the bow spring for biasing the bow spring from the first state to the second state.

12. A lancet device as in claim 1, wherein the lancet structure comprises a body extending from one side of an apex of the bow spring, and wherein lateral movement of the trigger into the housing causes a portion of the trigger to contact an opposing side of the apex of the bow spring to bias the bow spring to extend the lancet structure to the puncturing position.

13. A lancet device as in claim 1, wherein the trigger is releasably maintained in a first position with at least a portion of the trigger extending laterally out of the housing.

14. A lancet device as in claim 13, wherein the trigger is maintained in the first position through a connection which fractures upon lateral movement of the trigger into the housing.

15. The lancet device of claim 1, wherein the bow spring is supported within the housing between a first end and a second end.

16. A lancet device comprising:
    a housing including an interior cavity and an opening through the forward end;
    a lancet structure maintained within the interior cavity of the housing, the lancet structure comprising a bow spring having a puncturing tip extending therefrom, the bow spring in a first state maintaining the puncturing tip in a retracted position within the housing; and
    a trigger adapted for lateral movement into the housing so as to bias the bow spring from the first state to a second state thereby bending the bow spring and extending the puncturing tip through the forward end of the housing to achieve a puncturing position.

17. A lancet device as in claim 16, wherein lateral movement of the trigger into the housing biases the bow spring against its natural state to bend the bow spring and extend the puncturing tip to the puncturing position.

18. A lancet device as in claim 17, wherein continued lateral movement of the trigger into the housing subsequently releases the bias against the bow spring, permitting the bow spring to unbend and retract the puncturing tip to the retracted position.

19. A lancet device as in claim 18, wherein the trigger is maintained within the housing upon lateral movement of the trigger into the housing to a position in which the bias against the bow spring is released.

20. A lancet device as in claim 16, wherein the trigger is pivotable with respect to the housing, and wherein lateral movement of the trigger into the housing comprises pivoting the trigger with respect to the housing.

21. A lancet device as in claim 16, wherein the trigger comprises a cam surface for camming engagement with the bow spring for biasing the bow spring from the first state to the second state.

22. A lancet device as in claim 16, wherein the trigger is releasably maintained in a first position with at least a portion of the trigger extending laterally out of the housing through a connection which fractures upon lateral movement of the trigger into the housing.

23. A lancet device as in claim 22, wherein the lancet structure and the trigger are integrally molded as a single structure for assembly with the housing such that the bow spring is maintained within the housing with the puncturing tip extending toward the forward end and the trigger extends laterally from the housing out of the interior cavity of the housing and is connected to the bow spring through a connection which fractures.

24. The lancet device of claim 23, further comprising a cover integrally molded over the puncturing tip of the lancet structure.

25. The lancet device of claim 16, wherein the bow spring is supported within the housing between a first end and a second end.

* * * * *